United States Patent [19]

Sasaki et al.

[11] Patent Number: 4,796,605

[45] Date of Patent: Jan. 10, 1989

[54] INCUBATOR

[75] Inventors: Migaku Sasaki; Eiji Koike; Toshio Ohtomo; Jun Hirose, all of Urawa, Japan

[73] Assignee: ATOM Kabushiki Kaisha, Tokyo, Japan

[21] Appl. No.: 69,035

[22] Filed: Jul. 1, 1987

[30] Foreign Application Priority Data

Jul. 11, 1986 [JP] Japan .......... 61-163266
Jul. 11, 1986 [JP] Japan .......... 61-106447[U]
Jul. 11, 1986 [JP] Japan .......... 61-106448[U]

[51] Int. Cl.⁴ .......... A61B 19/00
[52] U.S. Cl. .......... 600/22
[58] Field of Search .......... 128/1 B, 30, 200.11, 128/203.16

[56] References Cited

U.S. PATENT DOCUMENTS 1,688,200 10/1928 Morgenthaler .......... 128/1 B
3,076,451 2/1963 Stoner .......... 128/1 B
3,187,744 6/1965 Dorsak et al. .......... 128/1 B
3,335,713 8/1967 Grosholz et al. .......... 128/1 B
3,821,947 7/1974 Schossow .......... 128/1 B
4,356,967 11/1982 Lunick .......... 128/1 B

*Primary Examiner*—Edward M. Coven
*Assistant Examiner*—J. P. Lacyk
*Attorney, Agent, or Firm*—James P. Ryther

[57] ABSTRACT

An incubator comprises an incubating chamber for accommodating an infant, and air supply means for supplying conditioned air into the incubating chamber. The air supply means comprises a dry passage and a wet passage which are partitioned from each other by a partition wall. The dry passage and the wet passage communicate by means of a first opening and a second opening, respectively, with the incubating chamber. The wet passage communicates by means of a connecting passage having an opening formed in a wall of the dry passage extended along the direction of air flow through the dry passage with the dry passage. A water tank containing water for humidifying air is provided in the connecting passage. A restricting means is provided at least for the first opening to regulate the flow rate of air that flows through the first opening.

9 Claims, 11 Drawing Sheets

| FIG. 1A |
|---|
| FIG. 1B |

| FIG. 4A | FIG. 4B |
|---|---|

INCUBATOR

BACKGROUND OF THE INVENTION

1. Field of the Invention

The present invention relates to an incubator suitable for use in protecting and caring for an immature infant such as a premature baby.

2. Description of the Prior Art

An incubator is used for protecting and caring for an immature or low birth weight infant such as a premature baby, in an optimum environment isolated from the atmosphere. Generally, the incubator comprises a base, a bed mounted on the base, and a transparent hood made of an acrylic resin or the like and covering the bed to define an incubating chamber isolated from the atmosphere. The temperature and humidity of the air within the incubating chamber are regulated so as to make the inside of the incubating chamber be an optimum condition for the infant accommodated therein. For example, the air within the incubating chamber is sucked into an air circulating system provided under the incubating chamber, and, when necessary, fresh air introduced from the outside of the incubator is mixed into the air sucked from the incubating chamber, and then the sucked or mixed air is warmed up and humidified properly, and the thus conditioned air is supplied into the incubating chamber. For this purpose, the air circulating system comprising an air mixing chamber in which the air sucked from the incubating chamber and fresh air introduced from the outside is mixed with each other, an air heating chamber in which the mixed air is warmed up properly, and a humidity regulating unit for regulating the humidity of the air heated in the air heating chamber. They are arranged in that order to constitute the air circulating system.

The humidity regulating unit has a dry passage through which the air warmed in the air heating chamber is supplied into the incubating chamber without being humidified, and a wet passage through which the air warmed in the air heating chamber is supplied into the incubating chamber after being humidified. The dry passage and the wet passage are arranged in parallel to each other along the direction of flow of air and are connected to the air heating chamber. The air warmed in the air heating chamber can be supplied through the dry passage into the incubating chamber without being humidified or through the wet passage into the incubating chamber after being humidified, or a part of the air warmed in the air heating chamber is supplied through the dry passage and the rest of the air is supplied through the wet passage into the incubating chamber.

In the conventional incubator, the dry passage and the wet passage are arranged in parallel to each other under the incubating chamber, and water for humidification is contained directly in the wet passage which is designed as a water tank integrally incorporated into the body of the incubator. Accordingly, to clean the water tank, the hood, bed and a partition plate separating the incubating chamber from the air circulating system must be removed, requiring troublesome cleaning work, which has been a significant disadvantage of the conventional incubator in view of the sanitary management of the incubator.

Furthermore, in the wet passage of the conventional incubator, air is unable to flow in satisfactory contact with water and hence, in some cases, the air is unable to be humidified sufficiently. That is, in the conventional incubator, the wet passage is connected directly to the air heating chamber and air is introduced to flow horizontally from the air heating chamber into the wet passage. Since water is contained in the lower part of the wet passage, the air inlet of the wet passage must be formed above the level of the surface of the water contained in the wet passage, and hence the air introduced from the air heating chamber through the air inlet into the wet passage flows horizontally within the wet passage toward the air outlet. Accordingly, the wet passage of the conventional incubator has the following problems.

The most part of the air introduced through the air inlet into the wet passage flows through the space above the surface of the water contained in the wet passage and only a small part of the air is able to flow in satisfactory contact with the water. Therefore, the water is not warmed up well by the heat of the air so the water is evaporated at a low rate. Consequently, the water flowing through the wet passage is unable to be humidified sufficiently.

To improve the humidifying capability, a conventional wet passage is provided with a plurality of deflectors to make air flow along a zigzag path defined by the deflectors. Since the deflectors increase the effective length of the wet passage and disturb the flow of air, the degree of contact of the air with water is increased to warm up the water to a higher extent and thereby the humidifying capability of the wet passage is improved. However, the deflectors increase the resistance of the wet passage against the flow of air to reduce the flow rate of air, so that the rate of supply of the humidified air into the incubating chamber is reduced.

SUMMARY OF THE INVENTION

Accordingly, it is an object o the present invention to provide an incubator having a high degree of freedom in designing the disposition and shape of humidifying water tank.

It is another object of the present invention to provide an incubator provided with a humidifying water tank easy to clean.

It is a further object of the present invention to provide an incubator capable of properly controlling the humidity of the air to be supplied into the incubating chamber and supplying sufficient humidified air into the incubating chamber.

To attain the above and other objects of the invention, the present invention provides an incubator comprising: an incubating chamber for accommodating an infant; air supply means for supplying air conditioned in temperature and humidity into the incubating chamber, the air supply means having a dry passage and a wet passage separated from each other by a partition wall, the dry passage communicating through a first opening with the incubating chamber, the wet passage communicating through a second opening with the incubating chamber and through a connecting passage having an opening formed in the wall of the dry passage extending along the direction of flow of air with the dry passage; a water tank for humidifying air provided in the connecting path; and restricting means provided at least at the first opening to control the flow rate of the air that flows through the first opening.

The above and further objects of the present invention will become obvious upon the understanding of the illustrative embodiments about to be described or will be indicated in the appended claims, and various advantages not referred to herein will occur to those skilled in the art upon employment of the invention in practice.

DETAILED DESCRIPTION OF THE PREFERRED EMBODIMENTS

Figures 1, 1A:
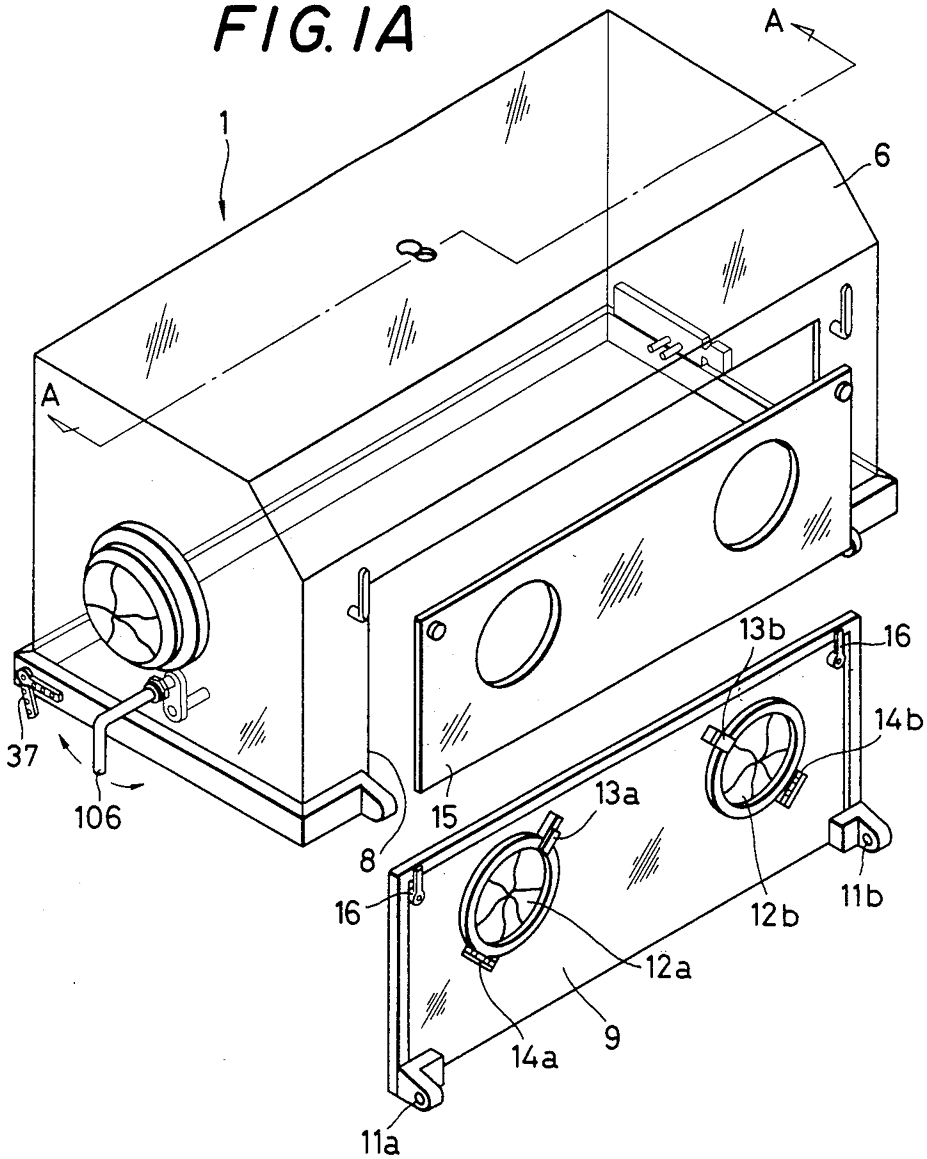
FIGS. 1A and 1B are an exploded perspective view of an incubator according to a preferred embodiment of the present invention, showing the general construction thereof.
Figure 1B:
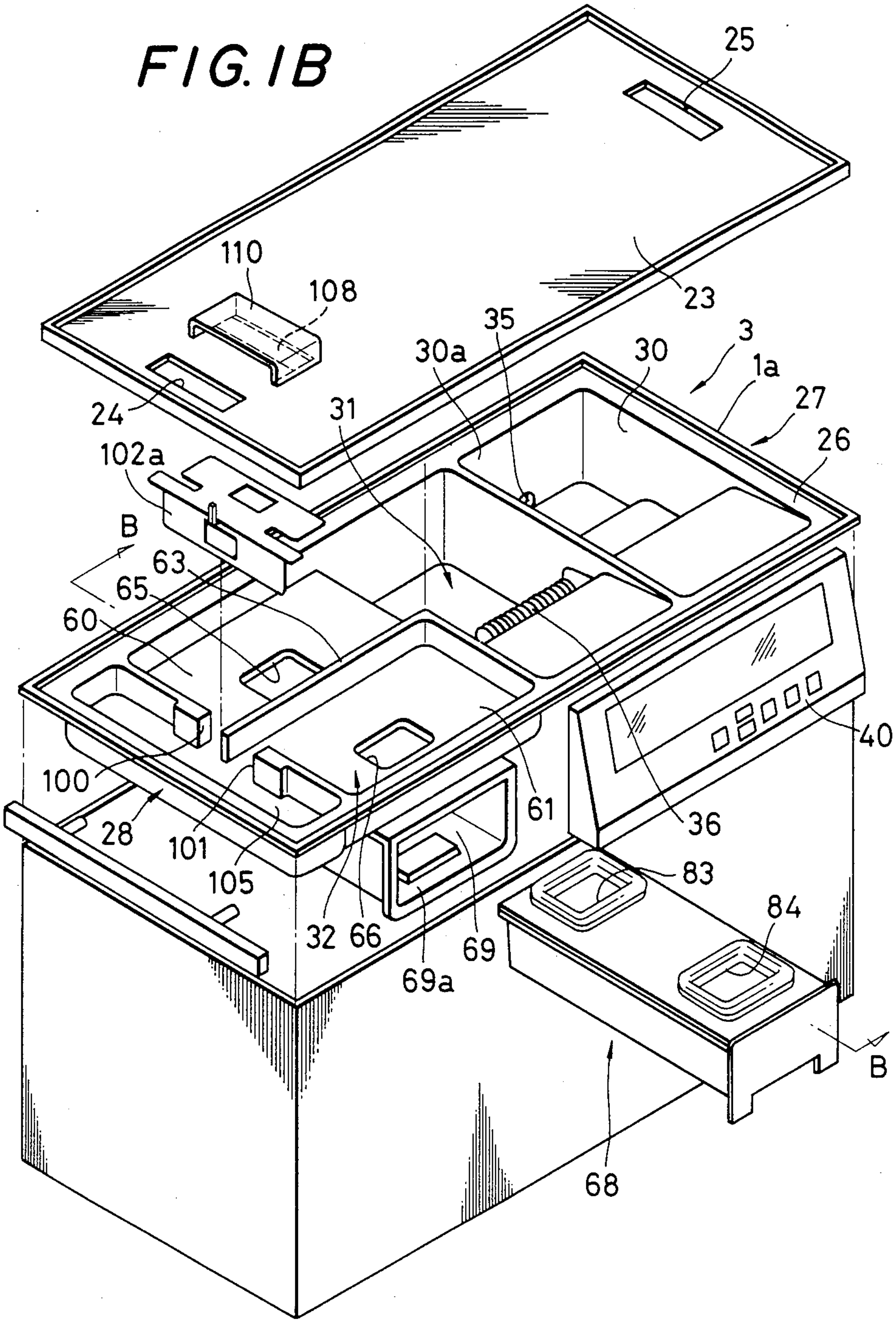
Figure 2:
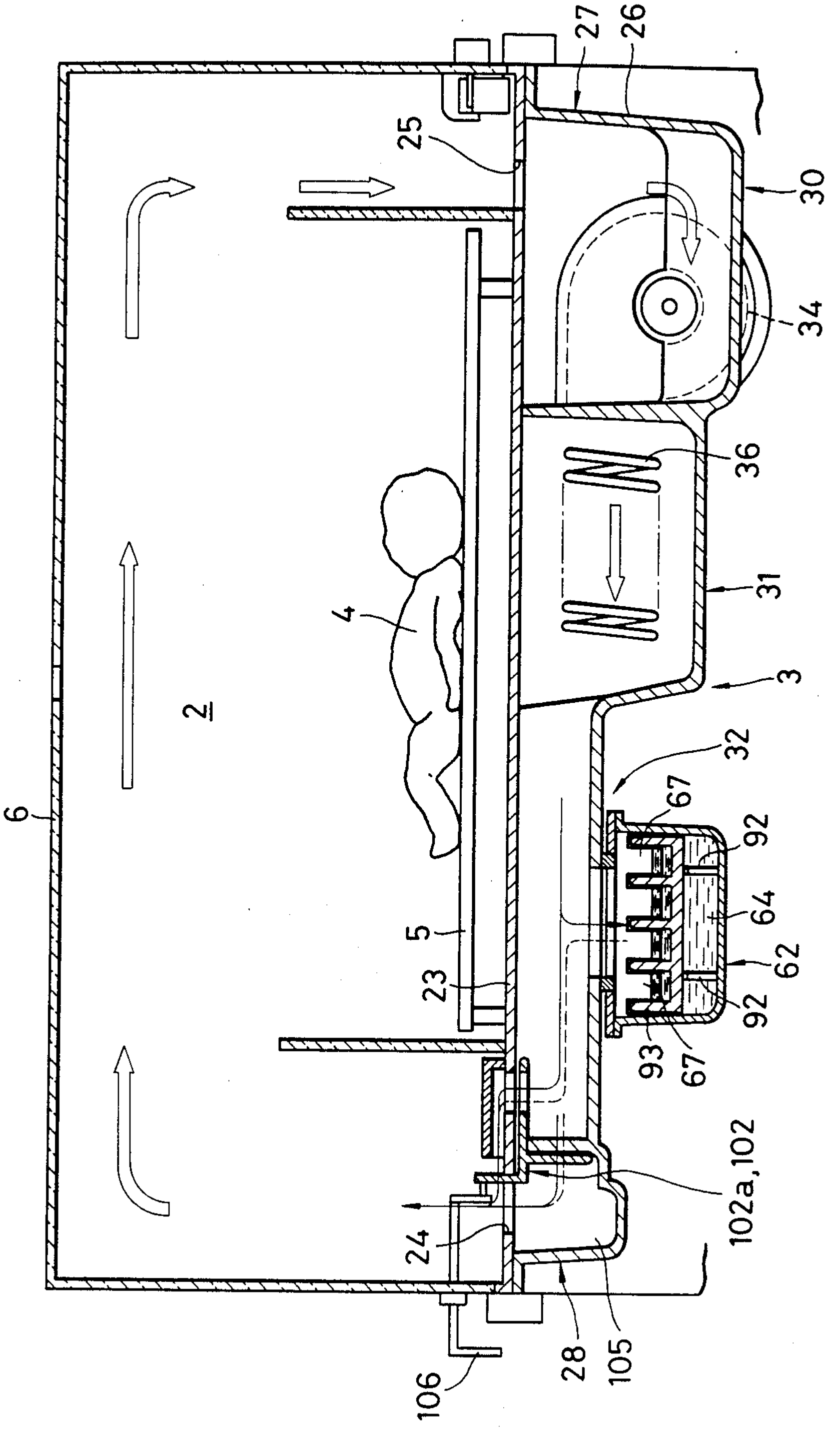
FIG. 2 is a sectional view taken on line A—A in FIG. 1A, showing the upper part of the incubator.

Referring to FIGS. 1A, 1B and 2, an incubating chamber 2 for isolating an infant 4 such as a premature baby, is provided in the upper part of an incubator 1, and has a bed 5 to lay the infant 4 therein and a hood 6 made of a transparent acrylic resin and covering the bed 5.

As shown in FIG. 1A, the hood 6 is formed in the shape of a bottomless box and is hinged with hinges 37 to an incubator body 1*a*. When necessary, the hood 6 is turned upward on the hinges 37 to open the incubating chamber 2. When necessary, the hood 6 can be easily removed from the incubator body 1*a*. A comparatively large rectangular opening 8 is formed in the front wall of the hood 6 to put in or to take out the infant therethrough. The opening 8 is convered with a door 9. Small circular doors 12*a* and 12*b* are provided on the door 9 to put hands into the incubating chamber 2 for the most part of the work for the treatment of the infant.

Referring to FIG. 2, when the hood 6 is closed, the incubating chamber 2 is isolated substantially perfectly from the atmosphere. Conditioned air is circulated through the incubating chamber 2 by an air circulating system 3 provided under the incubating chamber 2. The air circulating system 3 regulates the temperature and humidity of the air to be circulated through the incubating chamber 2. The air circulating system 3 has a fan 34 for circulating air, a heater 36 for warming up the air and a humidity regulating unit 32. The incubating chamber 2 is separated from the air circulating system 3 by a partition plate 23. An air inlet 24 and an air outlet 25 are formed in the partition plate 23 to supply air from the air circulating system 3 into the incubating chamber 2 and to suck out air from the incubating chamber 2.

Referring to FIG. 1B, a dry passage 60 and a wet passage 61 are arranged side by side in the humidity regulating unit 32 disposed in the lower section 28 of the air circulating system 3. The dry passage 60 communicates through a first opening 100 formed in the end wall thereof with the incubating chamber 2, while the wet passage 61 communicates through a second opening 101 formed in the end wall thereof with the incubating chamber 2. A partition wall 63 is provided between the dry passage 60 and the wet passage 61. The dry passage 60 communicates directly with the upper section 27 of the air circulating system 3, so that air flows directly from the upper section 27 into the dry passage 60, while the wet passage 61 communicates indirectly with the upper section 27, so that air is unable to flow directly from the upper section 27 into the wet passage 61.

Figure 3:
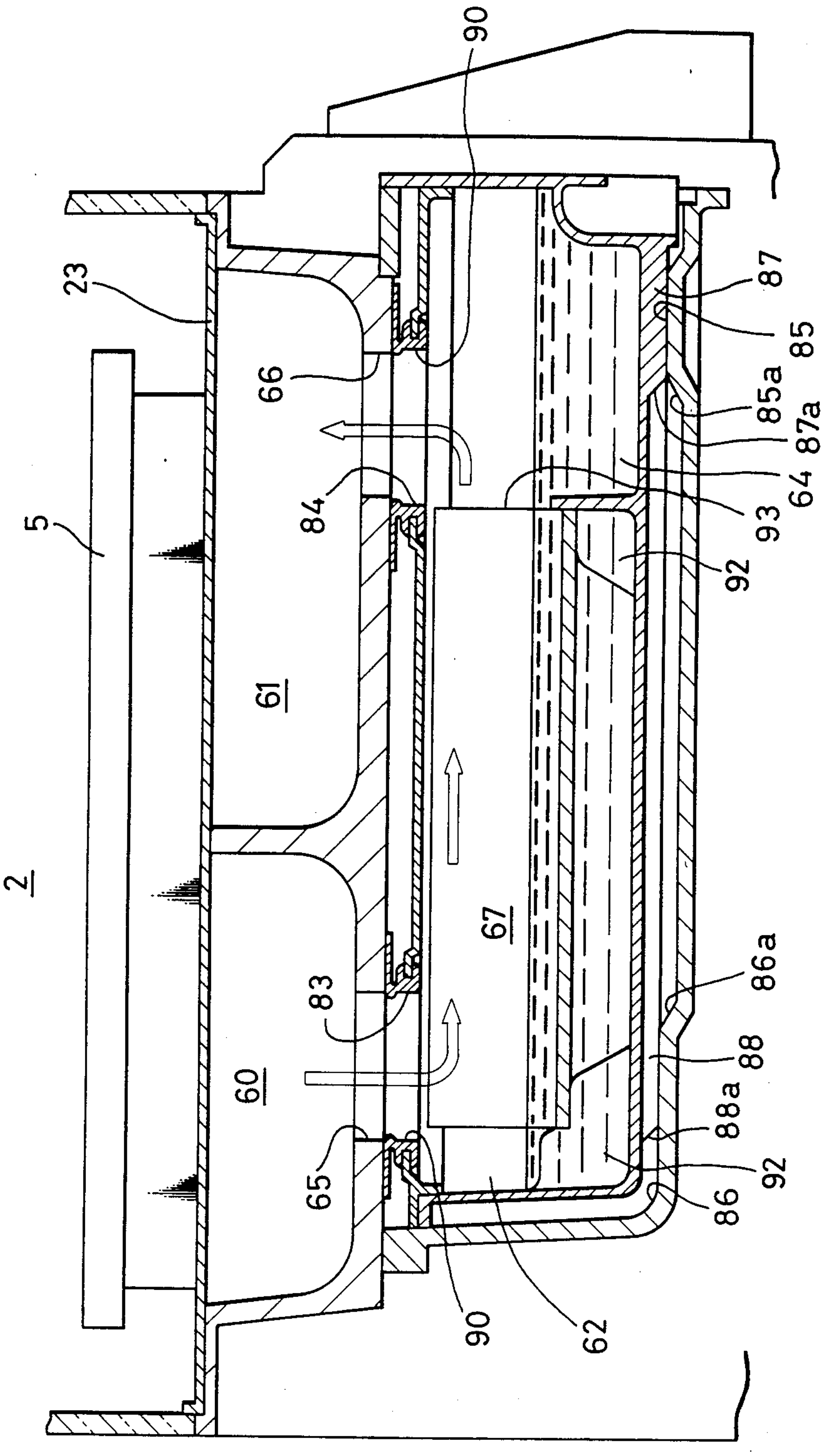
FIG. 3 is a sectional view taken on line B—B in FIG. 1B, showing the essential portion of the incubator.

Referring to FIGS. 1 to 3, a connecting passage 62 is provided below the dry passage 60 and the wet passage 61 to interconnect the dry passage 60 and the wet passage 61. The connecting passage 62 contains water 64 for humidification. The upper space of the connecting passage 62 serves as a humidifying chamber 67. An air outlet 65 to allow air to flow therethrough from the dry passage 60 into the connecting passage 62 is formed in the bottom wall of the dry passage 60, while an air inlet 66 to allow air to flow therethrough from the connecting passage 62 into the wet passage 61 is formed in the bottom wall of the wet passage 61.

It is important to form the air outlet 65 of the dry passage 60 in a wall extending in parallel to the direction of air flow in the dry passage 60. When the air outlet 65 is thus formed, all the air flows through the dry passage 60 and air flows scarcely into the connecting passage 62 when the opening 100 formed between the dry passage 60 and the incubating chamber 2 is opened fully by moving a humidify regulating plate 102*a*, namely, restricting means, which will be described hereinafter, so that air of a comparatively low humidity which has not been humidified at all is supplied into the incubating chamber 2.

On the other hand, when the open area of the opening 100 is reduced by operating the humidity regulating plate 102*a* to increase the resistance of the opening 100 against the air flow, a part of the air flowing through the air circulating system 3 flows into the connecting passage 62. Then the air flows through the wet passage 61 and an opening 101 formed between the wet passage 61 and the incubating chamber 2 into the incubating chamber 2 after being humidified in the connecting passage 62. Accordingly, in such a case, a mixture of air not humidified and flowing through the dry passage 60 and air humidified and flowing through the wet passage 61 is supplied into the incubating chamber 2.

Further, when the opening 100 between the dry passage 60 and the incubating chamber 2 is shut, all the air flowing through the dry passage 60 flows into the connecting passage 62, and then flows through the wet passage 61 into the incubating chamber 2 after being humidified in the connecting passage 62. In this case, the humidify within the incubating chamber 2 increases to the highest level.

Thus, the humidity within the incubating chamber is controlled by regulating the mixing ratio between the air not humidified that flows through the dry passage 60 and the air humidified that flows through the connecting passage 62 and the wet passage 61 by means of the humidity regulating plate 102*a* for regulating the degree of opening of the opening 100 between the dry passage 60 and the incubating chamber 2.

Figures 4, 4A:
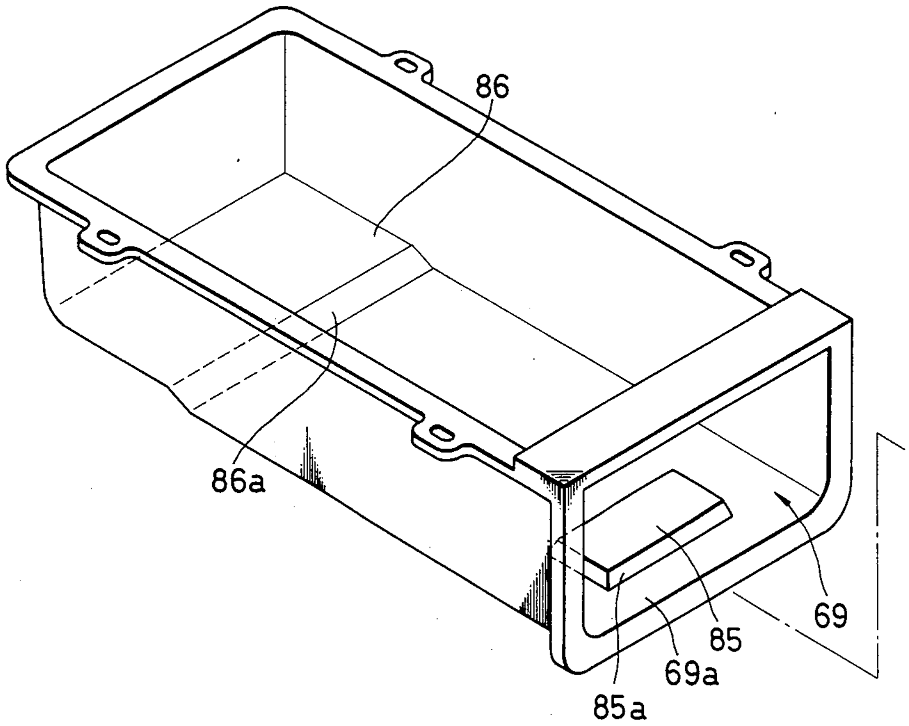
FIGS. 4A and 4B are an exploded perspective view of a humidifying tank unit for the incubator.

In this embodiment, the connecting passage 62 interconnecting the dry passage 60 and the wet passage 61 is of a sliding box type capable of being pulled out from or pushed into the incubator body 1*a*. As shown in FIGS. 1B and 4A, a rectangular receptacle 69 is provided in the front side of the incubator body 1*a*, and a humidifying tank unit 68 is received in the receptacle 69.

Figure 4B:
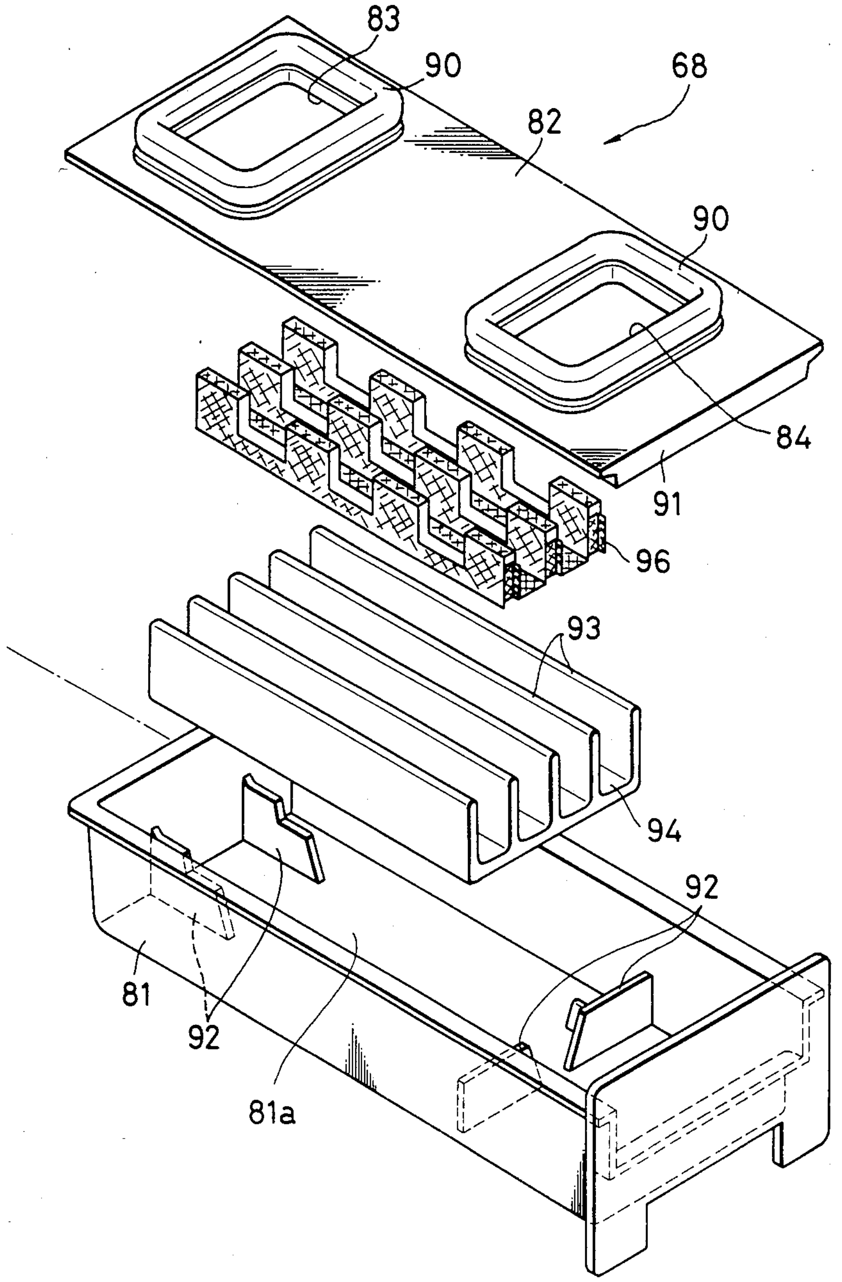

As best shown in FIG. 4B, the humidifying tank unit 68 has an elongate box-shaped water tank 81, and a lid 82 detachably put on the top of the water tank 81 with a projection 91 projecting from the lower surface thereof fitting the opening of the water tank 81.

Figure 6:
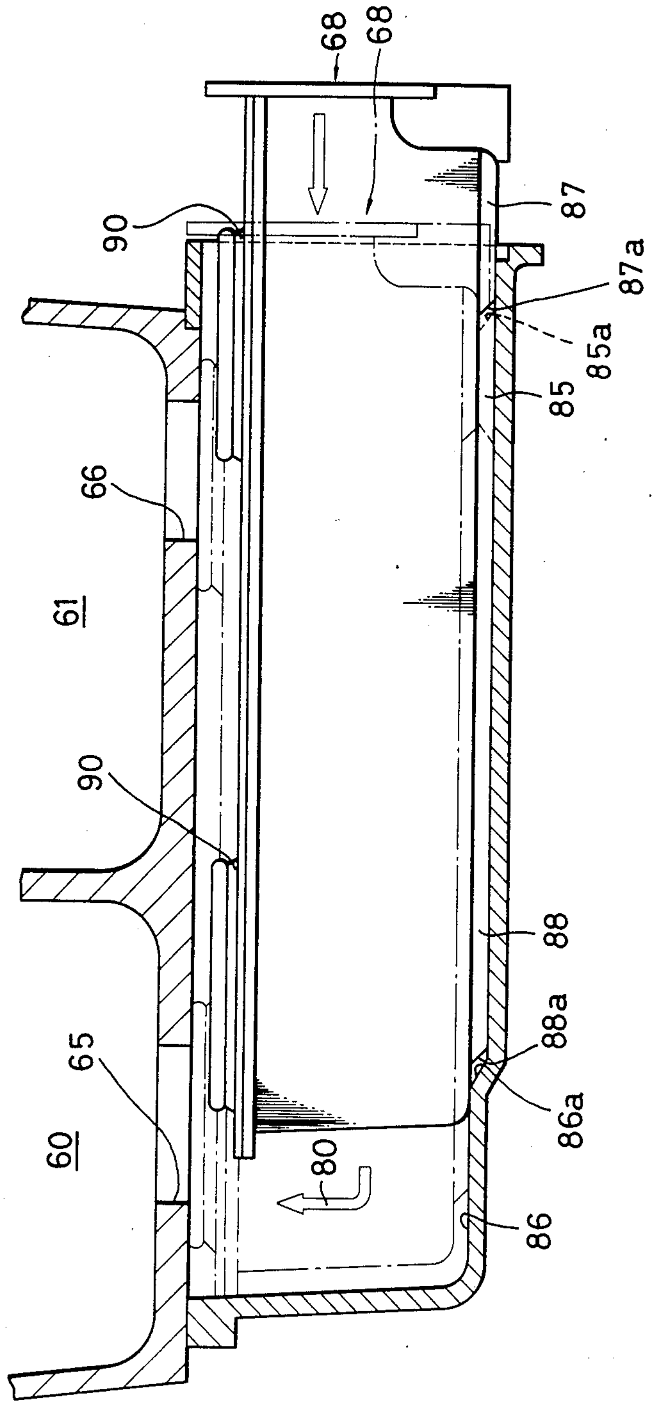
FIG. 6 is a sectional view of assistance in explaining a manner of mounting the humidifying tank unit on the incubator.

An air inlet 83 and an air outlet 84 are formed in the lid 82. As shown in FIGS. 3 and 6, the air inlet 83 and the air outlet 84 are formed at positions and in sizes so that the air inlet 83 and the air outlet 84 coincide with the air outlet 65 of the dry passage 60 and the air inlet 66 of the wet passage 61, respectively, when the humidifying tank unit 68 is put in place in the receptacle 69.

Figure 5:
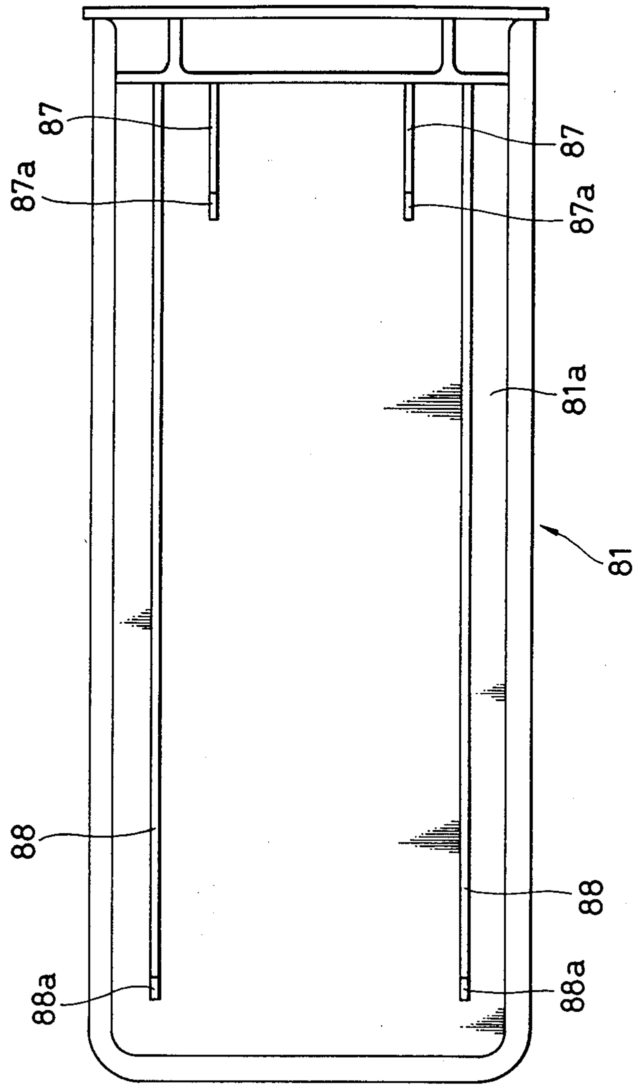
FIG. 5 is a bottom view of the humidifying tank unit.

Referring to FIGS. 4 to 6, guide means for raising the humidifying tank unit 68 upon the arrival of the humidifying tank 68 at the final position in the receptacle 69 is provided in the receptacle 69 and the humidifying tank unit 68. As best shown in FIG. 4A, a front land 85 and a rear land 86 for raising the humidifying tank unit 68 are formed in the bottom surface 69*a* of the receptacle 69 at the front and rear portions of the receptacle 69, respectively. The rear land 86 extends across the entire width of the receptacle 69 and has an inclined surface 86*a* formed in the front side thereof. On the other hand, the front land 85 is formed in the bottom surface of the receptacle 69 at the middle of the width of the receptacle 69 and has an inclined surface 85*a* formed in the front side thereof.

As shown in FIG. 5, a pair of inner ribs 87 which mount the front land 85 of the receptacle 69 to raise the water tank 81 in a direction indicated by an arrow 80 in FIG. 6 upon the arrival of the humidifying tank unit 68 at the final position, and a pair of outer ribs 88 which mount the rear land 86 of the receptacle 69 to raise the water tank 81 are formed in the outer surface of the bottom plate 81*a* of the water tank 81. As shown in FIGS. 5 and 6, the inner ribs 87 each has the shape of a rail and an inclined surface 87*a* formed at the free end thereof. The outer ribs 88 each also has the shape of a rail and an inclined surface 88*a* is formed at the free end thereof. The inner ribs 87 are formed between the outer ribs 88.

Referring to FIG. 6, since the distance between the outer ribs 88 is greater than the width of the front land 85, the outer ribs 88 do not mount the front land 85 in pushing the humidifying tank unit 68 in the receptacle 69, so that the humidifying tank unit 68 slides horizontally while being pushed in the receptacle 69.

As shown in FIG. 4B, in putting in the humidifying tank unit 68 in the receptacle 69, the side edges of a flange extending from the brim of the water tank 81 slide along the opposite side surfaces of the receptacle 69 to position the humidifying tank unit 68 with respect to lateral directions.

Since the side surfaces of the flange, the inner ribs 87 and the outer ribs 88 having the shape of a rail are in sliding contact with the inner surface of the receptacle 69 so that the contact area between the humidifying tank unit 68 and the receptacle 69 is small, only a small frictional resistance acts against the sliding movement of the humidifying tank unit 68 to enable smooth sliding movement of the humidifying tank unit 68 in pushing the same in the receptacle 69.

Referring to FIG. 6, when the humidifying tank unit 68 is pushed halfway in the receptacle 69, the outer ribs 88 formed in the bottom surface of the water tank 81 abut against the rear land 86 of the receptacle 69 and, substantially at the same time, the inner ribs 87 formed in the bottom surface of the water tank 81 abut against the front land 85 of the receptacle 69. As the humidifying tank unit 68 is pushed horizontally further into the receptacle 69, the inner ribs 87 and outer ribs 88 of the humidifying tank unit 68 are allowed to mount the corresponding lands 85 and 86 of the receptacle 69, respectively by the engagement of the inclined surfaces 87*a* of the inner ribs 87 with the inclined surface 85*a* of the front land 85 and the engagement of the inclined surfaces 88*a* of the outer ribs 88 with the inclined surface 86*a* of the rear land 86 to raise the humidifying tank unit 68.

In this embodiment, sealing members 90 formed of an elastic material such as a synthetic rubber, are provided on the lid 82 of the humidifying tank unit 68 so as to surround the air inlet 83 and the air outlet 84, respectively. Accordingly, when the humidifying tank unit 68 is raised in the receptacle 69, the sealing members 90 are pressed against the edges of the air outlet 65 and air inlet 66 of the incubator body 1*a*, respectively, to hermetically interconnect the air outlet 65 and the air inlet 83, and the air inlet 66 and the air outlet 84, respectively.

Thus, the humidifying tank unit 68 can be mounted on the incubator body 1*a* simply by pushing the same into the receptacle 69 of the incubator body 1*a*; the humidifying tank unit 68 is raised automatically in the final stage of the humidifying tank unit mounting operation, so that the air inlet 83 and air outlet 84 of the humidifying tank unit 68 are connected hermetically to the air outlet 65 and air inlet 66 of the incubator body 1*a*, respectively. Accordingly, the air to be supplied into the incubating chamber 2 will not leak from the air circulating path to reduce the amount of the air to be supplied into the incubating chamber 2 and the entrance of external dust and bacteria into the incubating chamber is obviated.

As shown in FIG. 4B, a plurality of supports 92 are provided upright on the bottom surface of the water tank 81 of the humidifying tank unit 68. A humidifying fin member is supported on the supports 92. The humidifying fin member is formed of a material having a high thermal conductivity such as aluminum, and has a base 94 and parallel fins 93 formed at regular intervals on the base 94.

The humidifying fin member serves for warming up the humidifying water 64 contained in the water tank 81. That is, the humidifying water 64 is put in the water tank 81 to a level slightly above the upper surface of the base 94 so that almost all the surfaces of the fins 93 of the humidifying fin member are exposed to the air supplied through the air inlet 83 into the humidifying tank unit 68. Accordingly, the heat of the air is transferred efficiently to the fins 93 of the humidifying fin member to warm up the humidifying fin member. Since the humidifying fin member is formed of a material having a high thermal conductivity such as aluminum, the heat transferred from the air to the fins 93 is transferred to the base 94 submerged in the humidifying water 64. Consequently, the humidifying water 64 is warmed up efficiently to a higher temperature by the base 94. The humidifying water 64 thus warmed-up evaporates briskly to increase the humidity in the upper space, namely, the humidifying chamber 67 (FIG. 3) of the connecting passage 62, so that the air that flows through the connecting passage 62 is humidified satisfactorily.

Furthermore, the provision of a humidifying pad 96 for covering the fins 93 of the humidifying fin member promotes the humidification of air. The humidifying pad 96 is formed of a highly water-absorptive porous material such as gauze, capable of absorbing the humidifying water 64 by the capillary effect thereof and holding the same. Accordingly, the air flowing through the humidifying chamber 67 is humidified also by the moisture evaporating from the humidifying pad 96 for sufficient humidification.

Thus, the present embodiment enhances the humidifying capability of the connecting passage 62 greatly without employing any deflector, and the fins 93 of the humidifying fin member extending along the direction of flow of air do not impede the flow of air. Consequently, air flows smoothly through the connecting passage 62 without reducing the flow rate of the humidified air to be supplied into the incubating chamber 2.

Furthermore, since the air inlet 83 of the humidifying tank unit 68 opens opposite the surface of the humidifying water 64 contained in the water tank 81 and hence the air is introduced through the inlet 83 perpendicularly to the surface of the humidifying water 64 contained in the water tank 81, the satisfactory contact of the air with the humidifying water 64 contained in the water tank 81 is possible to warm up the humidifying water 64 effectively, so that satisfactory humidification of the air is achieved.

The detachable lid 82 of the water tank 81 facilitates cleaning the interior of the humidifying tank unit 68, which is very advantageous from the view point of sanitary management. The water tank 81 need not necessarily be of such a construction provided with the lid 82; the humidifying tank unit 68 may be an integral member of the same function. When the humidifying tank unit 68 is an integral member, the same may be replaced with another one for cleaning.

Although the incubator in this embodiment has the air inlet 83 and the air outlet 84 formed separately in the lid 82 of the humidifying tank unit 68, and connected to the air outlet 65 of the dry passage 60 and to the air inlet 66 of the wet passage 61, respectively, the incubator need not be formed in such a construction; for example, a single opening connectable to both the air outlet 65 and the air inlet 66 may be formed in the upper wall of the water tank 81.

Furthermore, the guide means for raising the humidifying tank unit 68 as the same is pushed in the receptacle 69 need not necessarily be the ribs having the inclined surfaces formed in the water tank 81 and the lands formed in the receptacle 69, the guide means may comprise, for example, guide pins projecting from the opposite side surfaces of the water tank 81 of the humidifying tank unit 68, and guide grooves formed in the side surfaces of the receptacle 69 so as to receive the guide pins, respectively.

In this embodiment, the dry passage 60 and the wet passage 61 of the humidity regulating unit 32 are interconnected by the connecting passage 62, and a detachable humidifying tank unit 68 is provided separately within the connecting passage 62 so as to be removed from the receptacle 69, so that the humidifying tank unit 68 can be formed in a compact construction. The position and shape of the wet passage including the humidifying water tank for such an incubator is greatly dependent on the general design of the incubator. Accordingly, when the whole of the wet passage is designed to be removable from the incubator body, the size of the detachable part becomes large and inconvenient to handle it, which is undesirable from the viewpoint of sanitary management.

In this embodiment of the present invention, a connecting passage interconnects the dry passage and the wet passage, and the humidifying water tank is provided detachably in the connecting passage having a comparatively high degree of freedom in design. Accordingly, the detachable unit, namely, the water tank, can be formed in a compact construction and the detachable unit can be provided at a position apart from the incubating chamber.

The construction of the outlet section of the humidity regulating unit 32 will be described hereinafter with reference to FIGS. 1B, 2 and 7.

Figure 7:
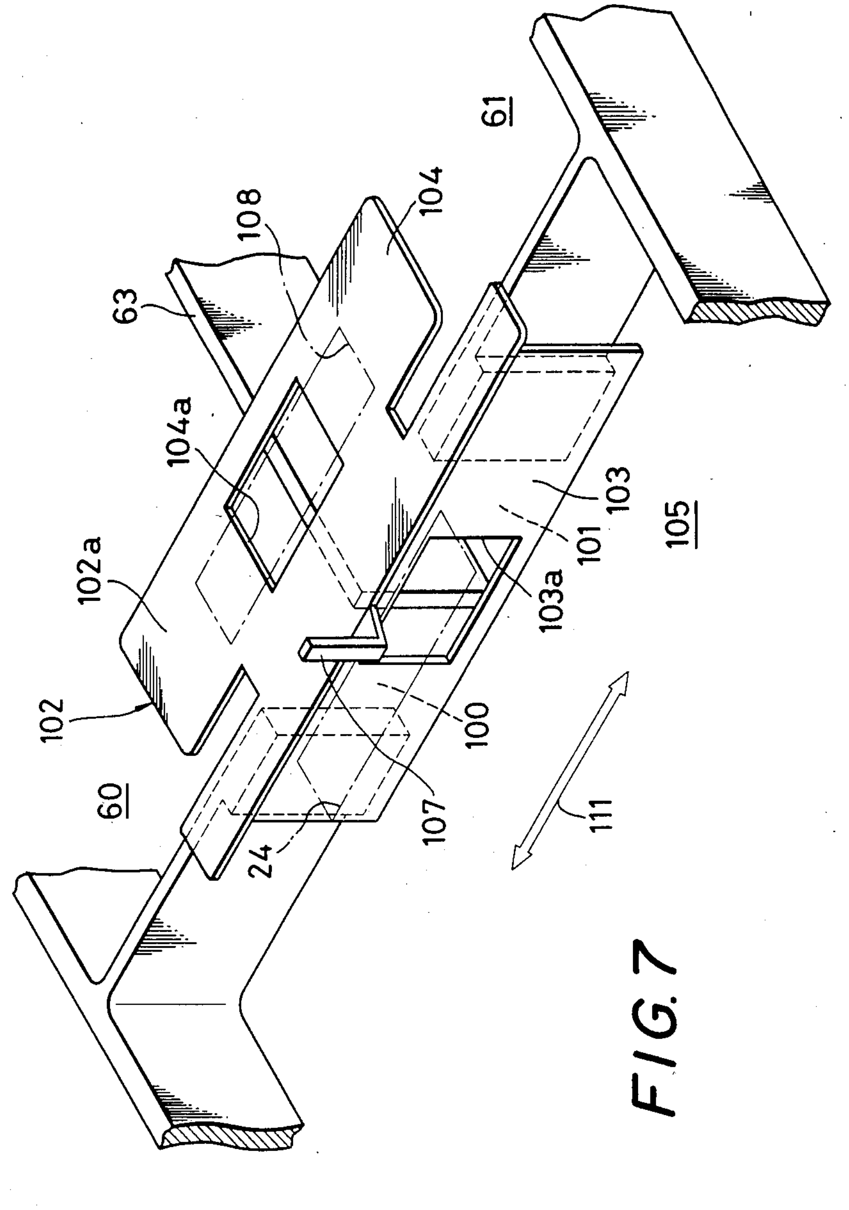
FIG. 7 is a perspective view showing the disposition of a humidity regulating plate.

Referring to FIGS. 1B and 7, a restricting means 102 is provided so as to extend between the first opening 100 of the dry passage 60 and the second opening 101 of the wet passage 61 of the humidity regulating unit 32. In this embodiment, the restricting means 102 consists of a sliding humidity regulating plate 102a extending between the openings 100 and 101.

The humidity of the air to be supplied into the incubating chamber 2 is regulated by sliding the humidity regulating plate 102a toward the side of the first opening 100 or toward the side of the second opening 101 as indicated by a double-head arrow 111. As shown in FIG. 7, the humidity regulating plate 102a has a substantially L-shaped cross section and consists of a vertical section 103 and a horizontal section 104. An opening 103a having the size substantially the same as those of the first opening 100 and the second opening 101 is formed in the central portion of the vertical section 103. When the humidity regulating plate 102a is shifted toward the side of the dry passage 60 to position the opening 103a exactly in front of the first opening 100, the second opening 101 is shut. On the contrary, when the humidity regulating plate 102a is shifted to the side of the wet passage 61 to position the opening 103a exactly in front of the second opening 101, the first opening 100 is shut. When the humidity regulating plate 102a is positioned in the middle between the dry passage 60 and the wet passage 61 so that the opening 103a coincides partially with the first opening 100 and partially with the second opening 101, the first opening 100 and the second opening 101 are opened by areas corresponding to the opening 103a, respectively. Thus, the mixing ratio between the air not humidified flowing through the first opening 100 of the dry passage 60 and the humidified air flowing through the second opening 101 of the wet passage 61 is varied to regulate the humidity of the air to be supplied into the incubating chamber 2.

As shown in FIG. 1A, a lever 106 for operating the humidity regulating plate 102a is extended rotatably through the wall of the hood 6 so that the inner end thereof engages with a projection 107 (FIG. 7) provided on the humidity regulating plate 102a. The lever 106 is turned to shift the humidity regulating plate 102a to the right or to the left by pushing the projection 107 with the inner end of the lever 106.

This embodiment employs the humidity regulating plate 102a capable of selectively restricting the flow of air through the first opening 100 and the flow of air through the second opening 101 as the restricting means 102. However, the restricting means 102 may be provided only for the first opening 100, namely, the outlet of the dry passage 60, because, as apparent from FIG. 1B, the resistance of the dry passage 60 against the flow of air is far lower than the combined resistance of the wet passage 61 and the connecting passage 62 against the flow of air. That is, when the first opening 100, namely, the outlet of the dry passage 60, is fully open, the air will not flow into the connecting passage 62 even if the second opening 101, namely, the outlet of the wet passage 61, is fully open, and all the air flows through the dry passage 60 and the first opening 100 into the incubating chamber 2. The ratio of the flow rate of the air that flows into the connecting passage 62 to the total fow rate of the air is dependent on the degree of restriction of the flow through the first opening 100. In some cases, the restricting means may be provided only at the second opening 101, namely, the outlet of the wet passage, depending on the respective constructions of the dry passage and the wet passage.

As shown in FIGS. 1B and 2, a mixing chamber 105 is provided between the dry passage 60 and wet passage 61 of the humidity regulating unit 32 and the incubating chamber 2. The mixing chamber 105 communicates by means of the first opening 100 with the dry passage 60 and by means of the second opening 101 with the wet passage 61. The mixing chamber 105 communicates also by means of a third opening, namely, the air inlet 24 formed in the partition plate 23 separating the incubating chamber 2 from the air circulating system 3, with the incubating chamber 2. Since the air inlet 24, namely, the third opening, is not formed opposite to neither the first opening 100 nor the second opening 101, the air not humidified and the humidified air are mixed well in the mixing chamber 105. For example, when the humidity regulating plate **102*a* is positioned in the middle between the dry passage 60 and the wet passage 61 to supply both of dry air which has not been humidified and having a comparatively low humidity and humidified air from the humidity regulating unit 32, the dry air and the humidified air are mixed well in the mixing chamber 105. Accordingly, air of uniform humidity is supplied into the incubating chamber 2 to make humidity distribution within the incubating chamber 2** uniform.

In a conventional incubator, the respective air outlets of the dry passage and wet passage of the air circulating system are opened directly into the incubating chamber, and a sliding humidity regulating plate is provided for these air outlets. In such an incubator, the position of an opening in each air outlet through which air is blown into the incubating chamber varies undesirably as the flow rate is varied by shifting the humidity regulating plate. For example, in supplying comparatively dry air into the incubating chamber, the humidity regulating plate is shifted to the side of the dry air outlet to open it, while, in supplying comparatively humid air into the incubating chamber, the humidity regulating plate is shifted to the side of the wet air outlet. Such variation of air blowing position causes irregular flow of air within the incubating chamber, and hence it is impossible to maintain the air in the vicinity of the infant such as a premature baby who is susceptible to change of temperature and humidity at a fixed temperature and at a fixed humidity. Furthermore, in simultaneously supplying both dry air and humid air into the incubating chamber, the humidity regulating plate is positioned in the middle between the dry air outlet and the wet air outlet to supply dry air through the dry air outlet and to supply humid air through the wet air outlet; consequently, it is liable that the dry air prevails in some part of the incubating chamber while the humid air prevails in the other part of the incubating chamber causing irregular humidity distribution within the incubating chamber.

In this embodiment of the present invention, the mixing chamber 105 is provided between the incubating chamber 2 and the dry passage 60 and wet passage 61. Accordingly, air is blown into the incubating chamber 2 from a fixed air blowing position regardless of the variation of the mixing ratio between the dry air and the humid air, and the dry air and the humid air are mixed well before being supplied into the incubating chamber 2.

As shown in FIG. 1B, in this embodiment, an auxiliary air inlet 108 is formed in the partition plate 23 near the air inlet 24, and a cover 110 is placed over the auxiliary air inlet 108. The auxiliary air inlet 108 is formed so as to extend over both the dry passage 60 and the wet passage 61, so that the dry passage 60 and the wet passage 61 communicate by means of the auxiliary air inlet 108 directly with the incubating chamber 2. As best shown in FIG. 7, the horizontal section 104 of the humidity regulating plate **102*a* extends below the auxiliary air inlet 108. The respective modes of direct communication of the dry passage 60 and the wet passage 61 with the incubating chamber 2 by means of the auxiliary air inlet 108 are regulated by an opening 104*a* formed in the horizontal section 104 of the humidity regulating plate 102*a* upon shifting the humidity regulating plate 102*a* for varying the respective degrees of opening of the first opening 100 and the second opening 101**.

As shown in FIG. 1B, the cover 110 is open only on the side thereof facing the air inlet 24 to direct the air blown through the auxiliary air inlet 108 toward the air inlet 24. Therefore, the air blown through the auxiliary air inlet 108 mixes with the air blown through the air inlet 24 before flowing into the incubating chamber 2. The air blown through the air inlet 24 flows upward in the incubating chamber 2, while the flow of the air blown through the auxiliary air inlet 108 joins perpendicularly to the flow of the former air. Accordingly, the confluence circulates through the incubating chamber 2 in a turbulent flow, for example, in a spiral flow. Therefore, in supplying both dry air and humid air into the incubating chamber 2, the dry air and the humid air are mixed well, and thereby the uniformity of the humidity distribution of the air supplied into the incubating chamber 2 is improved still further.

The mixing chamber 105 provided between the humidity regulating unit 32 and the incubating chamber 2 has a function to stabilize the flow of air within the incubating chamber 2 as well as a function to uniformize the humidity distribution in the air supplied into the incubating chamber 2. That is, although the respective flow speeds of the air supplied from the humidity regulating unit 32 at the first opening 100 and at the second opening 101 and blowing positions in the first opening 100 and in the second opening 101 are dependent on the condition of the air, namely, dry air, humid air or a mixture of dry air and humid air, the air is blown always from a fixed position into the incubating chamber 2 because the mixing chamber 105 is provided between the humidity regulating unit 32 and the incubating chamber 2. Consequently, a stable flow of air is produced within the incubating chamber 2 and a stable incubating environment for the infant 4 is established. The stable flow of air within the incubating chamber 2 enables accurate measurement of temperature and humidity in the incubating chamber 2 for steady temperature and humidity control.

The air to be supplied into the incubating chamber 2 flows from the upper section 27 toward the lower section 28 of the air circulating system 3. As shown in FIG. 1B, an air mixing chamber 30, the heating chamber 31 and the humidity regulating unit 32 are arranged in that order from the upper section 27 to the lower section 28 in an air conditioning casing 26.

As shown in FIGS. 1B and 2, a circulating fan 34 is provided in the air mixing chamber 30. A through hole 35 for taking fresh air into the air mixing chamber 30 is formed in the rear wall 30*a* of the air mixing chamber 30. An air filter (not shown) is provided in the through hole 35 to filter off dust and bacteria contained in the fresh air. When necessary, an oxygen cylinder is connected to the through hole 35 to supply oxygen-rich air into the incubating chamber 2.

The circulating fan 34 is for sucking fresh air and the air from the incubating chamber 2 into the air mixing chamber 30, and then supplying the air into the heating chamber 31. More concretely, the circulating fan 34 sends air from the air mixing chamber 30 into the air heating chamber 31 and thereby the pressure within the air mixing chamber is reduced to a negative pressure. Consequently, air is sucked through the air outlet 25 formed in the partition plate 23 into the air mixing chamber 30 and fresh air is sucked through the through hole 35 into the air mixing chamber 30, where the air from the incubating chamber 2 and the fresh air are mixed. Then, the mixed air is sent into the air heating chamber 31 by the circulating fan 34.

The mixed air is warmed in the air heating chamber 31 up to a predetermined temperature by the heater 36. The heater 36 is controlled by a control unit 40 provided on the front panel of the incubator body 1*a* on the basis of data detected by a detecting unit 38 shown in FIG. 8.

Figure 8:
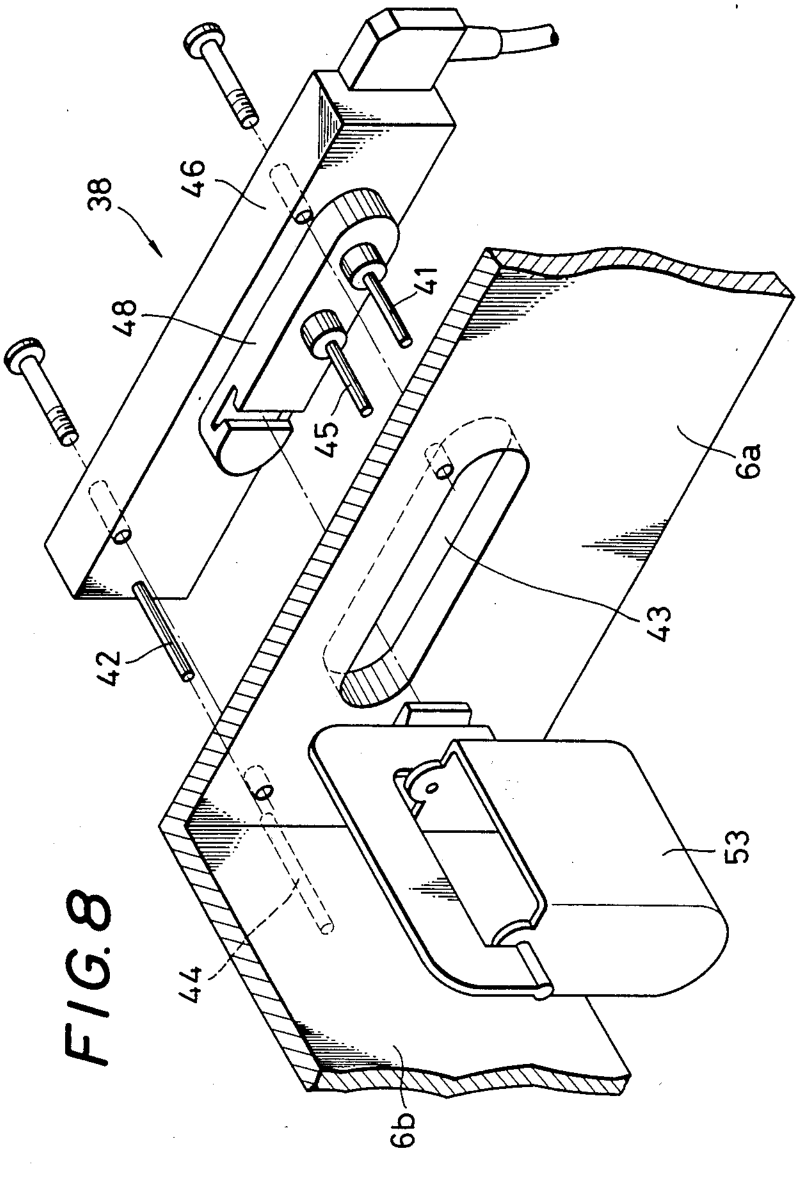
FIG. 8 is a perspective view of a sensing unit.

The detecting unit 38 will be described briefly with reference to FIG. 8. The detecting unit 38 comprises an elongate casing 46, a temperature sensor 41, a wall temperature sensor 42, and a humidity sensor 45. The sensors 41, 42 and 45 are attached to the casing 46. The detecting unit 38 is attached to one side wall 6*a* of the hood 6 covering the incubating chamber 2. The temperature sensor 41 and the humidity sensor 45 are inserted through an opening 43 formed in the side wall 6*a* in the incubating chamber 2. The wall temperature sensor 42 is inserted in a wall temperature detecting hole 44 formed in the rear wall 6*b* of the hood 6 to detect the temperature of the rear wall 6*b*. A water pot 53 is attached to the casing 46 of the detecting unit 38. A piece of gauze or the like immersed in the water contained in the water pot 53 is wound on the humidity sensor 45 to detect humidity in a well-known manner. Data acquired by the detecting unit 38 is given to the control unit 40 and is displayed on the display of the control unit 40. The heater 36 for warming up air and the humidity regulating plate 102*a* of the humidity regulating unit 32 are controlled manually or automatically on the basis of the data.

As illustrated in FIG. 1A, the infant 4 is put in or taken out from the incubating chamber 2 through the opening 8 formed in the front wall of the hood 6 covering the incubating chamber 2. The opening 8 is covered with the door 9 hinged to the hood 6 with hinges 11*a* and 11*b* so as to be turned outside on the hinges 11*a* and 11*b* to open the opening 8. When the door 9 is opened, the bed 5 (FIG. 2) can be pulled outside the incubating chamber 2. The small doors 12*a* and 12*b* provided on the door 9 can be turned on hinges 14*a* and 14*b* to be opened to the right and to the left after unfastening latches 13*a* and 13*b*, respectively. When necessary, the small doors 12*a* and 12*b* are opened to insert hands through openings respectively covered with these small doors 12*a* and 12*b* into the incubating chamber 2.

Figure 9:
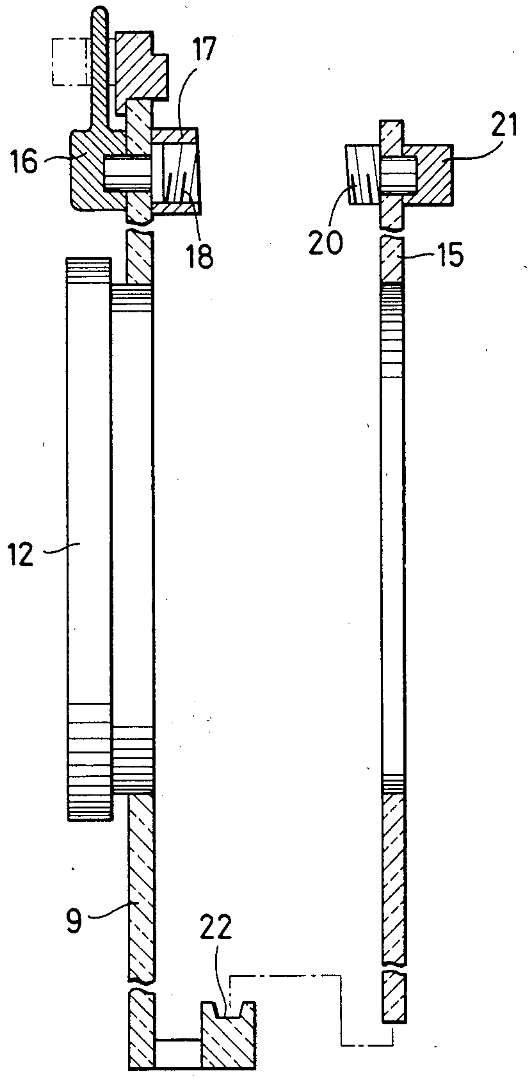
FIG. 9 is a sectional view of assistance in explaining a manner of attachment of a front panel.

The incubator 1 shown in FIG. 1A is of a double-wall type capable of improved warm keeping performance, provided with a transparent front panel 15 attached to the inner side of the door 9 in a manner as shown in FIG. 9. Referring to FIG. 9, latches 16 for locking the door 9 at the closed position are supported pivotally on pins 17 attached to the door 9, respectively. Internal threads 18 are formed in the respective inner ends of the pins 17. Pins 21 each having one end provided with an external thread 20 are attached to the upper right-hand corner and upper left-hand corner of the front panel 15, respectively. The respective externally threaded ends of the pins 21 are screwed in the respective internally threaded ends of the pins 18 to fasten the upper portion of the front panel 15 to the door 9, while the lower side of the front panel 15 is inserted in a groove 22 formed at the bottom of the door 9 to fasten the front panel 15 to the door 9. Such a manner of fastening the front panel 15 to the inner side of the door 9 requires only a few parts to fasten the front panel 15 neatly to the door 9. Although the internal threads 18 are formed on the pin 17 while the external threads 20 are formed on the pins 20, the internal threads and external threads may be formed on the pin 20 and the pin 17, respectively.

In this embodiment, the air outlet 65 and the air inlet 66 are formed in the respective bottom walls of the dry passage 60 and the wet passage 61, respectively, the receptacle is provided under the dry passage 60 and the wet passage 61, and the humidifying tank unit 68 is accommodated in the receptacle 69. However, the humidifying tank unit may be provided at other position when the disposition of the dry passage and wet passage of the air circulating system requires. For example, in an incubator provided with an air circulating system having a dry passage and a wet passage placed one over the other, a humidifying tank unit may be detachably attached to the side of the air circulating system by suitable means.

As apparent from the foregoing description, according to the present invention, since the dry passage and wet passage of the air circulating system communicate with each other by means of the connecting passage interconnecting the dry passage and the wet passage, and the connecting passage is used also as a water tank for containing water for humidifying the air to be supplied into the incubating chamber, the degree of freedom of designing the disposition and shape of the water tank is increased. Accordingly, the water tank can be disposed at a position to facilitate cleaning the water tank, the water tank can be formed in a shape facilitating cleaning the same, and the water tank can be cleaned easily.

Furthermore, the connecting passage can be formed so as to enable the air that flows therethrough to flow in satisfactory contact with the water contained therein for humidification transferring a sufficient amount of heat to the water to cause brisk evaporation of the water. Accordingly, the air is humidified sufficiently while flowing through the connecting passage having a moderate length, and hence the humidification of the air to be supplied into the incubating chamber does not reduce the flow rate of the humidified air.

As many apparently widely different embodiments of this invention may be made without departing from the spirit and scope thereof, it is to be understood that the invention is not limited to the specific embodiments thereof except as defined in the appended claims.

What is claimed is:

1. An incubator consisting of an incubator body, an incubating chamber located above the incubator body for accommodating an infant, air supply means disposed below the incubating chamber for supplying heated and humidified air to said incubating chamber, and a partition plate for partitioning said air supply means from said incubating chamber, said air supply means comprising:

means for providing air flow through the air supply means from an upstream location to a downstream location;

a heating chamber provided with heating means for warming the air to be supplied to said incubating chamber;

a dry chamber located downstream from and communicating with said heating chamber, said dry chamber having a bottom arranged parallel to the direction of air flow;

a wet chamber arranged adjacent to said dry chamber and having a bottom arranged parallel to the direction of air flow;

a first partition wall arranged perpendicular to the air flow for preventing air flow between said wet chamber and said heating chamber and said dry chamber;

a water tank disposed below said dry chamber and said wet chamber and containing humidifying water;

an outlet opening formed in the bottom of said dry chamber for communicating said dry chamber with said water tank;

an inlet opening formed in the bottom of said wet chamber for communicating said wet chamber with said water tank;

a mixing chamber arranged downstream from said dry chamber and said wet chamber;

a second partition wall arranged perpendicular to said flow of air for preventing flow of air between said mixing chamber from said dry chamber and said wet chamber, said second partition wall having a first opening formed therein for communicating said dry chamber with said mixing chamber and a second opening formed therein for communicating said wet chamber with said mixing chamber;

first restricting means for regulating the flow rate of the air through said first opening; and an air outlet provided in said partition plate for communicating said incubating chamber with said heating chamber and an air inlet provided in said partition plate adjacent said mixing chamber for communicating said mixing chamber with said incubating chamber.

2. An incubator according to claim 1, wherein said air supply means further comprises an air mixing chamber arranged between and communicating with said air outlet and said heating chamber, said air mixing chamber also communicating with an external source of air such that air taken from said air outlet is mixed with air from said external source.

3. An incubator according to claim 1, wherein an auxiliary air inlet is provided in said partition plate communicating with said dry chamber and said wet chamber and having a cover which is open only in the direction facing said air inlet, and second restricting means for regulating the flow rates of air from said dry chamber and said wet chamber through said auxiliary air inlet.

4. An incubator according to claim 3, wherein said first restricting means is operatively connected with said second restricting means.

5. An incubator according to claim 4, wherein said first and second restricting means are formed on an L-shaped sliding member.

6. An incubator according to claim 1 wherein said water tank is detachably received in a receptacle formed in said incubator body and having one opening connected to said outlet opening of said dry chamber and another opening connected to said inlet opening of said wet chamber when said tank is in said receptacle.

7. An incubator according to claim 6, wherein said receptacle includes guide means for guiding said tank into said receptacle in both the horizontal and vertical directions such that an air-tight connection occurs between said openings in the tank and said outlet opening and said inlet opening.

8. An incubator according to claim 7, wherein said guide means includes inclined surfaces formed on the tank and receptacle.

9. An incubator according to claim 6, wherein a sealing means is provided around said openings.

* * * * *